(12) United States Patent
Sacks

(10) Patent No.: US 12,070,420 B2
(45) Date of Patent: *Aug. 27, 2024

(54) DIRECT SELECTIVE LASER TRABECULOPLASTY

(71) Applicant: BELKIN VISION LTD., Yavne (IL)

(72) Inventor: Zachary Sacks, Modiin (IL)

(73) Assignee: BELKIN VISION LTD., Yavne (IL)

( * ) Notice: Subject to any disclaimer, the term of this patent is extended or adjusted under 35 U.S.C. 154(b) by 0 days.

This patent is subject to a terminal disclaimer.

(21) Appl. No.: 17/735,153

(22) Filed: May 3, 2022

(65) Prior Publication Data
US 2022/0257414 A1    Aug. 18, 2022

Related U.S. Application Data

(63) Continuation of application No. 17/254,279, filed as application No. PCT/IB2019/055564 on Jul. 1, 2019.
(Continued)

(51) Int. Cl.
*A61F 9/008* (2006.01)
*A61B 90/00* (2016.01)
*A61F 9/007* (2006.01)

(52) U.S. Cl.
CPC .............. *A61F 9/008* (2013.01); *A61B 90/04* (2016.02); *A61F 9/0079* (2013.01);
(Continued)

(58) Field of Classification Search
CPC .... A61F 9/008; A61F 9/0079; A61F 9/00823; A61F 2009/00868; A61F 2009/00891; A61B 90/04; A61B 2090/049
(Continued)

(56) References Cited

U.S. PATENT DOCUMENTS

| | | |
|---|---|---|
| 5,049,147 A | 9/1991 | Danon |
| 5,141,506 A | 8/1992 | York |

(Continued)

FOREIGN PATENT DOCUMENTS

| | | |
|---|---|---|
| CN | 102193182 A | 9/2011 |
| CN | 105138996 A | 12/2015 |

(Continued)

OTHER PUBLICATIONS

Gophotonics, "NL200 series," Data Sheet, pp. 1-3, Jun. 29, 2017.
(Continued)

*Primary Examiner* — Aaron F Roane
(74) *Attorney, Agent, or Firm* — MEITAR PATENTS LTD.

(57) ABSTRACT

A system includes a radiation source, one or more beam-directing elements, and a controller. The controller is configured to cause the radiation source to emit one or more aiming beams at the beam-directing elements such that the aiming beams are directed, by the beam-directing elements, toward an eye of a patient, to verify that each of the aiming beams is properly directed by the beam-directing elements, and, in response to verifying that each of the aiming beams is properly directed by the beam-directing elements, to treat the eye by causing the radiation source to irradiate one or more target regions of the eye with respective treatment beams. Other embodiments are also described.

20 Claims, 4 Drawing Sheets

Related U.S. Application Data

(60) Provisional application No. 62/692,868, filed on Jul. 2, 2018, provisional application No. 62/739,238, filed on Sep. 30, 2018, provisional application No. 62/748,461, filed on Oct. 21, 2018.

(52) U.S. Cl.
CPC .... *A61F 9/00823* (2013.01); *A61B 2090/049* (2016.02); *A61F 2009/00868* (2013.01); *A61F 2009/00891* (2013.01)

(58) Field of Classification Search
USPC .......................................................... 606/6
See application file for complete search history.

(56) References Cited

U.S. PATENT DOCUMENTS

| | | |
|---|---|---|
| 5,151,909 A | 9/1992 | Davenport et al. |
| 5,422,899 A | 6/1995 | Freiberg et al. |
| 6,414,980 B1 | 7/2002 | Wang et al. |
| 6,761,713 B2 | 7/2004 | Teichmann |
| 8,160,113 B2 | 4/2012 | Adams et al. |
| 11,382,794 B2 * | 7/2022 | Sacks ..................... A61F 9/008 |
| 2003/0179344 A1 | 9/2003 | Van de Velde |
| 2003/0225398 A1 | 12/2003 | Zepkin et al. |
| 2005/0185138 A1 | 8/2005 | Wong et al. |
| 2005/0197655 A1 | 9/2005 | Telfair et al. |
| 2006/0100677 A1 | 5/2006 | Blumenkranz et al. |
| 2008/0167642 A1 | 7/2008 | Palanker et al. |
| 2008/0234667 A1 | 9/2008 | Lang et al. |
| 2008/0255546 A1 | 10/2008 | Orbachevski |
| 2009/0247997 A1 | 10/2009 | Watanabe et al. |
| 2010/0057059 A1 | 3/2010 | Makino |
| 2011/0172649 A1 | 7/2011 | Schuele et al. |
| 2012/0259321 A1 | 10/2012 | Vera et al. |
| 2013/0317570 A1 | 11/2013 | Luttrull et al. |
| 2016/0008169 A1 | 1/2016 | Yu |
| 2017/0127938 A1 | 5/2017 | Izatt et al. |
| 2017/0184875 A1 | 6/2017 | Newman |
| 2018/0104477 A1 | 4/2018 | Kurtz et al. |
| 2018/0221199 A1 | 8/2018 | Heacock |
| 2018/0235462 A1 | 8/2018 | Gooi et al. |
| 2019/0105200 A1 | 4/2019 | Hipsley |
| 2019/0117459 A1 | 4/2019 | Berlin |
| 2020/0038245 A1 | 2/2020 | Hart et al. |
| 2020/0078216 A1 | 3/2020 | Raksi |
| 2020/0093639 A1 | 3/2020 | McCall, Jr. |
| 2020/0352785 A1 | 11/2020 | Holland et al. |
| 2021/0338484 A1 | 11/2021 | Hipsley |
| 2023/0201037 A1 | 6/2023 | Barrett et al. |
| 2023/0226372 A1 | 7/2023 | Herekar et al. |

FOREIGN PATENT DOCUMENTS

| | | |
|---|---|---|
| CN | 205698218 U | 11/2016 |
| EP | 3329839 A1 | 6/2018 |
| JP | 2007151739 A | 6/2007 |
| JP | 2016013255 A | 1/2016 |
| JP | 2018051210 A | 4/2018 |
| WO | 9416425 A1 | 7/1994 |
| WO | 9515134 A1 | 6/1995 |
| WO | 0195842 A1 | 12/2001 |
| WO | 02087442 A1 | 11/2002 |
| WO | 2006119349 A2 | 11/2006 |
| WO | 2006128038 A2 | 11/2006 |
| WO | 2008118198 A2 | 10/2008 |
| WO | 2010094353 A1 | 8/2010 |
| WO | 2011017002 A2 | 2/2011 |
| WO | 2013059564 A1 | 4/2013 |
| WO | 2014025862 A1 | 2/2014 |
| WO | 2014191031 A1 | 12/2014 |
| WO | 2015069197 A1 | 5/2015 |
| WO | 2015130821 A2 | 9/2015 |
| WO | 2016058931 A2 | 4/2016 |
| WO | 2016156760 A1 | 10/2016 |
| WO | 2016187436 A1 | 11/2016 |
| WO | 2017023296 A1 | 2/2017 |
| WO | 2018152020 A1 | 8/2018 |
| WO | 2020018242 A1 | 1/2020 |
| WO | 2021026538 A1 | 2/2021 |
| WO | 2021170664 A1 | 9/2021 |
| WO | 2022223690 A1 | 10/2022 |

OTHER PUBLICATIONS

EP Application # 20201567.3 Office Action dated Jun. 6, 2023.
JP Application # 2020561860 Office Action dated Jun. 13, 2023.
JP Application # 2021516473 Office Action dated Jun. 20, 2023.
CN Application # 2020800563096 Office Action dated Jul. 1, 2023.
EP Application # 20864109.2 Search Report dated Aug. 10, 2023.
Gazzard et al., "Selective Laser Trabeculoplasty versus Drops for Newly Diagnosed Ocular Hypertension and Glaucoma: The LiGHT RCT," Health Technology Assessment, NHS, vol. 23, issue 31, pp. 1-132, Jun. 2019.
Kelley et al., "Stem Cells in the Trabecular Meshwork: Present and Future Promises," Experimental Eye Research, vol. 88, issue 4, pp. 747-751, Apr. 2009.
Dueker et al., "Stimulation of Cell Division by Argon and Nd:YAG Laser Trabeculoplasty in Cynomolgus Monkeys," Investigative Ophthalmology & Visual Science, vol. 31, No. 1, pp. 115-124, year 1990.
Nowell et al., "Corneal Epithelial Stem Cells and their Niche at a Glance," Cell Science at a Glance, vol. 130, issue 6, pp. 1021-1025, year 2017.
Kim et al., "Diagnosis of Corneal Limbal Stem Cell Deficiency," Current Opinion in Ophthalmology, Wolters Kluwer Health, Inc., vol. 28, No. 4, pp. 355-362, Jul. 2017.
Gonzalez et al., "Limbal Stem Cells: Identity, Developmental Origin, and Therapeutic Potential," WIREs Developmental Biology, Wiley, vol. 7, issue 2, pp. 1-23, Mar. 2018.
Sepehr, "Corneal Endothelial Cell Dysfunction: Etiologies and Management," Therapeutic Advances in Opthalmology, pp. 1-19, year 2018.
Espana et al., "Existence of Corneal Endothelial Slow-Cycling Cells," Investigative Ophthalmology & Visual Science, vol. 56, No. 6, pp. 3827-3837, Jun. 2015.
Walshe et al., "Serial Explant Culture Provides Novel Insights into the Potential Location and Phenotype of Corneal Endothelial Progenitor Cells," Experimental Eye Research, vol. 127, pp. 9-13, year 2014.
Pinnamaneni et al., "Concise Review: Stem Cells in the Corneal Stroma," Stem Cells, vol. 30, issue 6, pp. 1059-1063, year 2012.
SG Application # 11202010437T Office Action dated May 13, 2022.
U.S. Appl. No. 16/935,236 Office Action dated Jun. 16, 2022.
EP Application # 19877990.2 Search Report dated Jul. 5, 2022.
U.S. Appl. No. 16/935,236 Office Action dated Nov. 7, 2022.
EP Application # 20769533.9 Search Report dated Nov. 8, 2022.
AU Application # 2020345067 Office Action dated Nov. 30, 2022.
CN Application # 201980070459X Office Action dated Dec. 23, 2022.
"Smart Selecta Duet—Your Smart Selection for Glaucoma Care," Product Brochure, pp. 1-6, The Lumenis Group of Companies, year 2018.
CN Application # 2019800436416 Office Action dated Aug. 17, 2022.
U.S. Appl. No. 16/935,236 Office Action dated Sep. 15, 2022.
U.S. Appl. No. 16/420,194 Office Action dated Aug. 5, 2022.
CN Application # 2020800163407 Office Action dated Feb. 4, 2023.
JP Application # 2020561860 Office Action dated Feb. 7, 2023.
Root, "How to perform a Laser Iridotomy (Video)," pp. 1-14, year 2010, as downloaded from https://timroot.com/how-to-perform-a-laser-iridotomy-video/.
AU Application # 2022211843 Office Action dated Sep. 27, 2023.
AU Application # 2021311097 Office Action dated Sep. 28, 2023.
U.S. Appl. No. 17/427,926 Office Action dated Oct. 17, 2023.
JP Application # 2021536316 Office Action dated Oct. 24, 2023.
JP Application # 2020561860 Office Action dated Oct. 31, 2023.

(56) References Cited

OTHER PUBLICATIONS

JP Application # 2021516473 Office Action dated Nov. 7, 2023.
SG Application # 11202010437T Office Action Dec. 5, 2023.
International Application # PCT/IB2023/060104 Search Report Dec. 26, 2023.
U.S. Appl. No. 17/136,052 Office Action dated Dec. 22, 2023.
U.S. Appl. No. 17/427,926 Office Action dated Dec. 22, 2023.
Danielson et al., Fixed High-Energy versus Standard Titrated Energy Settings for Selective Laser Trabeculoplasty, Journal of Glaucoma Publish Ahead of Print, Wolters Kluwer Health, Inc., pp. 1-16, year 2023.
Radcliffe et al., "Energy Dose-Response in Selective Laser Trabeculoplasty: A Review," Journal of Glaucoma, vol. 31, pp. e49-e68, year 2022.
Gazzard, "A Brief Guide to Gonioscopy," Video Clip, Optometry today, pp. 1-2, May 21, 2015, as downloaded from https://www.youtube.com/watch?v=8yTTbHWxUik.
Alward et al., "Principles of Gonioscopy," Color Atlas of Gonioscopy, American Academy of Opthalmology, pp. 1-10, Nov. 8, 2017, as downloaded from https://www.aao.org/education/disease-review/principles-of-gonioscopy.
Nolan et al., "Gonioscopy skills and techniques," Community Eye Health Journal, vol. 34, No. 112, pp. 40-42, year 2021.
Breazzano et al., "Analysis of Schwalbe's Line (Limbal Smooth Zone) by Scanning Electron Microscopy and Optical Coherence Tomography in Human Eye Bank Eyes," Journal of Ophthalmic and Vision Research, vol. 8, issue 1, pp. 9-16, Jan. 2013.
Thorlabs, Inc., "CPS520—Collimated Laser Diode Module, 520 nm, 4.5 mW, Elliptical Beam, Ø11 mm," Product Details, pp. 1-1, years 1999-2023, as downloaded from https://www.thorlabs.com/thorproduct.cfm?partnumber=CPS520.
Prophotonix, "Green Laser Modules," Product Information, pp. 1-8, year 2024, as downloaded from https://www.prophotonix.com/led-and-laser-products/laser-modules/laser-modules-color/green-laser-modules/.
Idex Helath & Science LLC, "532 nm StopLine® single-notch filter," Product Details, pp. 1-2, year 2023 as downloaded from https://www.idex-hs.com/store/product-detail/nf03_532e_25/fl-009362?cat_id=products&node=individual_optical_filters.
Brackley et al., "Lecture: Using the Slit Lamp Microscope to Visualize the Ocular Structures," Video Clip, pp. 1-2, Sep. 17, 2022, as downloaded from https://www.youtube.com/watch?v=1E-sEhy9tBo.
Bruce et al., "Zoom in on Gonioscopy," Review of Optometry, pp. 1-8, Sep. 1, 2016, as downloaded from https://www.reviewofoptometry.com/article/zoom-in-on-gonioscopy.
AU Application # 2022211843 Office Action dated Jan. 8, 2024.
JP Application # 2022508451 Office Action dated Mar. 5, 2024.
AU Application # 2021369792 Office Action dated Mar. 21, 2024.
International Application # PCT/IB2023/061472 Search Report dated Feb. 29, 2024.
U.S. Appl. No. 17/427,926 Office Action dated May 9, 2024.
EP Application # 19877990.2 Office Oction dated May 13, 2024.
EP Application # 24158977.9 Search Report dated May 15, 2024.
EP Applicatian # 21845437.9 Search Report dated Jun. 19, 2024.
JP Application # 2023217477 Office Action dated Jul. 9, 2024.
U.S. Appl. No. 17/273,323 Office Action dated Jun. 18, 2024.

* cited by examiner

DIRECT SELECTIVE LASER TRABECULOPLASTY

CROSS-REFERENCE TO RELATED APPLICATIONS

The present application is a continuation of U.S. application Ser. No. 17/254,279, filed Dec. 20, 2020 in the national phase of International Application PCT/IB2019/055564, filed Jul. 1, 2019, which claims the benefit of (i) U.S. Provisional Appl. No. 62/692,868, entitled "Direct laser selective trabeculoplasty Process (DSLT) and Safeties," filed Jul. 2, 2018, (ii) U.S. Provisional Appl. No. 62/739,238, entitled "Eye tracking flash illumination," filed Sep. 30, 2018, and (iii) U.S. Provisional Appl. No. 62/748,461, entitled "Crossed ranging beams," filed Oct. 21, 2018. The respective disclosure of each of the aforementioned references is incorporated herein by reference.

FIELD OF THE INVENTION

The present invention relates to ophthalmological devices and methods for the treatment of glaucoma, ocular hypertension (OHT), and other diseases.

BACKGROUND

In a trabeculoplasty procedure, a radiation source irradiates the trabecular meshwork in an eye of a patient with one or more treatment beams, thus lowering the intraocular pressure in the eye.

Geffen, Noa, et al., "Transscleral selective laser trabeculoplasty without a gonioscopy lens," Journal of glaucoma 26.3 (2017): 201-207 describes a study to investigate results of selective laser trabeculoplasty (SLT) performed directly on the sclera without a gonioscopy lens.

US Patent Application Publication 2015/0366706 to Belkin, whose disclosure is incorporated herein by reference, describes an apparatus including a probe and a processor. The probe is positioned adjacent to an eye of a patient and is configured to irradiate a trabecular meshwork of the eye with one or more optical beams. The processor is configured to select one or more target regions of the trabecular meshwork, and to control the probe to irradiate the selected target regions with the optical beams.

SUMMARY OF THE INVENTION

There is provided, in accordance with some embodiments of the present invention, a system including a radiation source and a controller. The controller is configured to display a live sequence of images of an eye of a patient, and, while displaying the sequence of images, cause the radiation source to irradiate the eye with one or more aiming beams, which are visible in the images. The controller is further configured to, subsequently to causing the radiation source to irradiate the eye with the aiming beams, receive a confirmation input from a user, and, in response to receiving the confirmation input, treat the eye by causing the radiation source to irradiate respective target regions of the eye with a plurality of treatment beams.

In some embodiments, the system further includes:
a focusing lens; and
one or more beam-directing elements,
and the controller is configured to cause the radiation source to irradiate the eye with the treatment beams by
firing the treatment beams at the beam-directing elements through the focusing lens, such that the beams are focused by the focusing lens prior to being directed, by the beam-directing elements, toward the respective target regions.

In some embodiments, the aiming beams impinge on at least part of each of the target regions.

In some embodiments, the controller is further configured to superimpose, on each of the images, a marker passing through each of the target regions.

In some embodiments, the marker is elliptical.

In some embodiments, at least part of each of the target regions is located within 1 mm of a limbus of the eye.

In some embodiments, the controller is further configured to:
superimpose a marker on each of the images, and
prior to treating the eye, by processing the images, verify respective positions of the aiming beams with respect to the marker,
and the controller is configured to treat the eye in response to verifying the positions of the aiming beams.

In some embodiments, the controller is configured to verify the positions of the aiming beams by verifying that the aiming beams overlap the marker.

In some embodiments, the controller is configured to verify the positions of the aiming beams by verifying that the aiming beams lie outside the marker.

In some embodiments, the controller is configured to treat the eye such that respective edges of the treatment beams impinge on respective portions of the eye over which the marker is superimposed.

In some embodiments, the marker is elliptical.

In some embodiments, the controller is further configured to:
prior to displaying the live images, display a still image of the eye,
identify an elliptical portion of the eye in the still image, based on input from the user, and
in response to identifying the elliptical portion of the eye, superimpose an elliptical marker over the elliptical portion of the eye in each of the images.

In some embodiments, the controller is configured to superimpose the elliptical marker over the elliptical portion of the eye by:
subsequently to identifying the elliptical portion of the eye, identifying an offset from a center of a limbus of the eye to a center of the elliptical portion in the still image, and
for each image of the images:
identifying the center of the limbus in the image, and
superimposing the elliptical marker on the image such that the center of the elliptical marker is at the identified offset from the center of the limbus.

In some embodiments, the controller is configured to identify the elliptical portion of the eye by:
displaying, over the still image, (i) the elliptical marker, and (ii) a rectangle circumscribing the elliptical marker, and
subsequently to displaying the elliptical marker and the rectangle, in response to the user adjusting the rectangle, adjusting the elliptical marker such that the elliptical marker remains circumscribed by the rectangle, until the elliptical marker is superimposed over the portion of the eye.

In some embodiments, the controller is further configured to identify a limbus of the eye in the still image, and the controller is configured to display the elliptical marker over the limbus.

In some embodiments, the system further includes a camera configured to:
acquire the images, and
acquire a still image of the eye, prior to acquiring the images,
and the controller is further configured to:
based on the still image of the eye, identify a static region in a field of view of the camera that includes a pupil of the eye, and
treat the eye such that each of the treatment beams impinges on the eye outside the static region.

In some embodiments, the system further includes one or more beam-directing elements,
the controller is configured to treat the eye by aiming the beam-directing elements at the target regions in sequence and firing the treatment beams at the beam-directing elements, and
the controller is further configured to inhibit the beam-directing elements from being aimed at the static region even while none of the treatment beams is being fired.

In some embodiments, the controller is configured to identify the static region by:
receiving, from the user, a limbus-locating input indicating a location of the limbus in the still image, and
identifying the static region based on the location of the limbus.

In some embodiments,
the images are first images and the aiming beams are first aiming beams,
the system further includes a camera configured to acquire multiple second images of the eye while treating the eye, and
the controller is configured to treat the eye by iteratively:
verifying a position of a respective second aiming beam in the second image, and
in response to the verifying, firing a respective one of the treatment beams at the eye.

In some embodiments, the controller is configured to verify the position by verifying that a distance between the second aiming beam and a respective one of the target regions is less than a predefined threshold.

In some embodiments, the controller is configured to fire the respective one of the treatment beams at the respective one of the target regions.

In some embodiments, the system further includes an illumination source, and the controller is further configured to cause the illumination source to intermittently flash visible light at the eye such that the light illuminates the eye at least during respective acquisitions of the second images.

In some embodiments, a peak average intensity of the light over a duration of each of the flashes is between 0.003 and 3 $mW/cm^2$.

In some embodiments, the controller is configured to cause the illumination source to flash the light at a frequency of at least 60 Hz.

In some embodiments, the frequency is at least 100 Hz.

In some embodiments, the system further includes an illumination source, and the controller is further configured to cause the illumination source to illuminate the eye with near-infrared light at least during respective acquisitions of the second images.

In some embodiments, the controller is further configured to cause the illumination source to intermittently flash visible light at the eye while treating the eye.

In some embodiments, the system further includes an optical unit including the radiation source and a plurality of beam emitters,
and the controller is further configured to, prior to causing the radiation source to irradiate the eye with the aiming beams, cause the beam emitters to shine a plurality of range-finding beams on the eye, the range-finding beams being shaped to define different respective portions of a predefined composite pattern such that the predefined composite pattern is formed on the eye only when the optical unit is at a predefined distance from the eye.

In some embodiments, the range-finding beams are shaped to define two perpendicular shapes, and the predefined composite pattern includes a cross.

In some embodiments, the system further includes an optical unit including the radiation source, and the controller is configured to cause the radiation source to irradiate the target regions while the optical unit is directed obliquely upward toward the eye and the eye gazes obliquely downward toward the optical unit.

In some embodiments, the system further includes a wedge, and the optical unit is directed obliquely upward toward the eye by virtue of being mounted on the wedge.

There is further provided, in accordance with some embodiments of the present invention, a system, including a wedge, an optical unit mounted on the wedge such that the optical unit is directed obliquely upward, the optical unit including a radiation source, and a controller. The controller is configured to treat an eye of a patient by causing the radiation source to irradiate respective target regions of the eye with a plurality of treatment beams while the eye gazes obliquely downward toward the optical unit.

There is further provided, in accordance with some embodiments of the present invention, a method including displaying a live sequence of images of an eye of a patient. The method further includes, while displaying the sequence of images, irradiating the eye with one or more aiming beams, which are visible in the images. The method further includes, subsequently to irradiating the eye with the aiming beams, receiving a confirmation input from a user, and in response to receiving the confirmation input, treating the eye by irradiating respective target regions of the eye with a plurality of treatment beams.

The present invention will be more fully understood from the following detailed description of embodiments thereof, taken together with the drawings, in which:

DETAILED DESCRIPTION OF EMBODIMENTS

Overview

Figure 1:
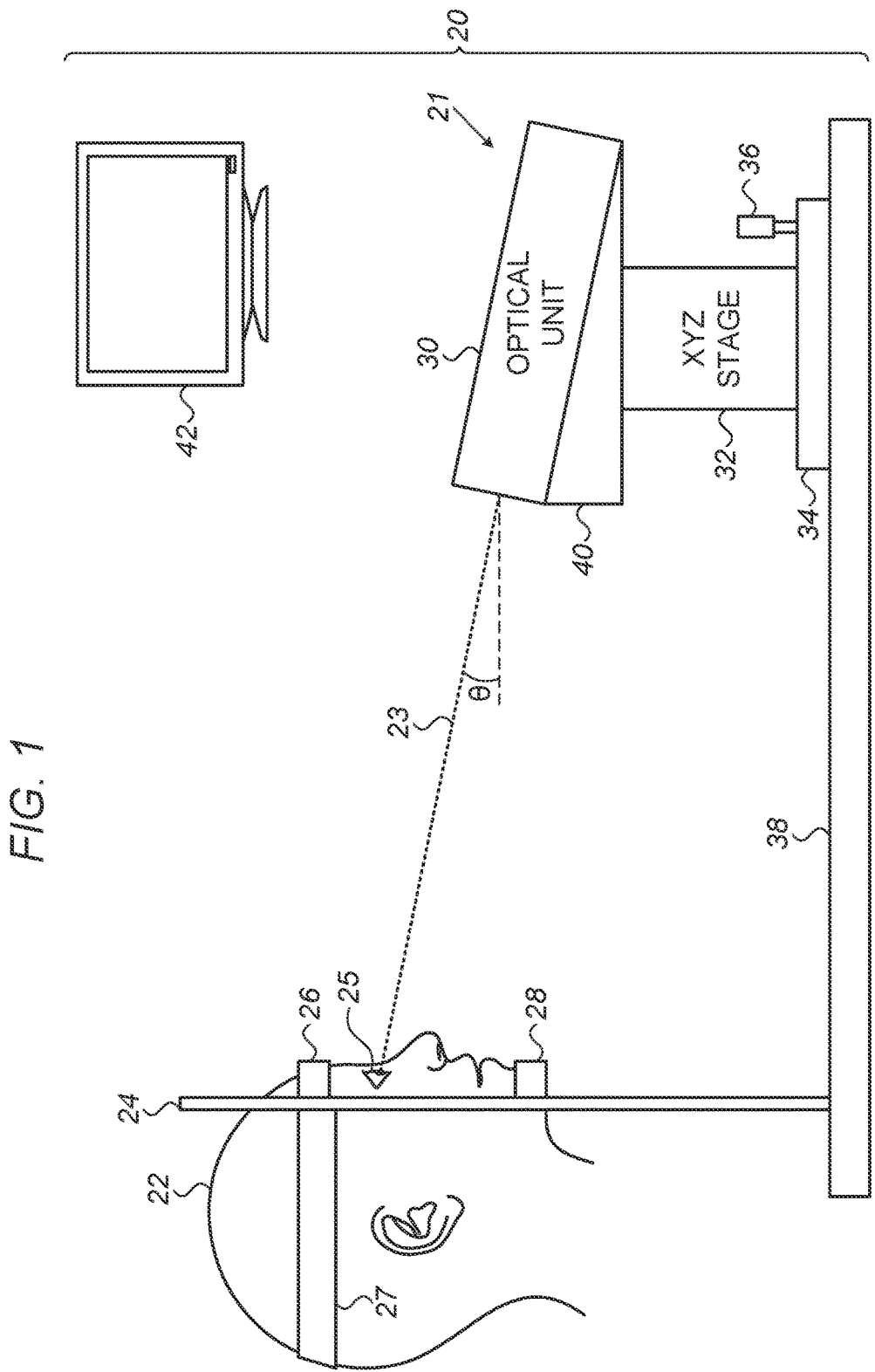
FIG. 1 is a schematic illustration of a system for performing a trabeculoplasty, in accordance with some embodiments of the present invention.

Embodiments of the present invention provide an automated trabeculoplasty device configured to perform a trabeculoplasty procedure on an eye safely and efficiently. The trabeculoplasty device comprises a controller and an optical unit, which comprises a radiation source, a camera, and beam-directing elements. As described in detail below, the controller is configured to control the radiation source and the beam-directing elements in response to feedback from the camera, such that the beam-directing elements direct beams of radiation, which are emitted by the radiation source, toward the appropriate locations on the eye. The emitted beams of radiation include both treatment beams, which irradiate the trabecular meshwork of the eye, and aiming beams, which are used to help aim the treatment beams.

Typically, prior to the procedure, the controller displays a live video of the eye in which two ellipses are superimposed over the eye: an inner ellipse, which marks the limbus of the eye, and an outer ellipse, displaced from the inner ellipse by a small distance, which passes through or near each of the target regions that are to be irradiated by the treatment beams. The controller further simulates the procedure by sweeping an aiming beam over the outer ellipse, typically such that the aiming beam impinges on at least part of each target region. Advantageously, this simulation may help the physician visualize the path along the eye that is to be targeted by the treatment beams, i.e., the path along which the target regions lie. After the physician confirms the targeted path along the eye, the controller causes the radiation source to fire the treatment beams at the target regions.

It is noted that since each beam of radiation generally impinges on the eye with a non-infinitesimal spot size, the present application generally describes each beam as impinging on a "region" of the eye, whose area is a function of the spot size, rather than impinging at a "point" on the eye. Thus, for example, the present application refers to "target regions," rather than "target points." Nonetheless, in the context of the present application, including the claims, references to calculating the location of a target region may refer to implicitly calculating the location of the region by calculating the location of a single point within the region, such as the point at the center or edge of the region at which the center or edge (respectively) of the beam is to be aimed. (Even if, subsequently, the center or edge of the beam deviates slightly from the calculated point, the present application, including the claims, may consider the beam to have impinged on the calculated target region.)

Typically, prior to simulating the procedure as described above, the controller acquires a still image of the eye, and identifies the limbus in the still image. The controller then superimposes the aforementioned inner ellipse over the limbus. Subsequently, the controller allows the physician to modify the position and/or shape of the inner ellipse, such that the inner ellipse marks the limbus per the physician's definition thereof. (Since the limbus is generally not well defined, the location of the limbus per the physician may differ slightly from the location automatically identified by the controller.) For example, the controller may circumscribe the inner ellipse by a rectangle, and then allow the physician to adjust the ellipse by dragging the sides or corners of the circumscribing rectangle.

As the present inventors have observed, the trabecular meshwork may be irradiated most effectively when the treatment beams impinge on the eye at or near the limbus, which may be identified by the user as described above or automatically identified by the controller. Hence, in some embodiments of the present invention, the controller causes the radiation source to target the limbus or a portion of the eye near the limbus. For example, at least part of each target region may be located within 1 mm (e.g., within 400 microns) of the limbus. As a specific example of the above, the center of each target region may be located within 1 mm (e.g., within 400 microns) of the limbus, such that the center of each treatment beam impinges on the eye within 1 mm (e.g., within 400 microns) of the limbus.

During both the simulated treatment and the actual treatment, the camera acquires images of the eye at a relatively high frequency (e.g., at a frequency greater than 40 Hz or 50 Hz), and the controller tracks motion of the eye by identifying the center of the limbus in each of the acquired images. In response to identifying the center of the limbus, during the simulated treatment, the controller may move the inner and outer ellipses such that the inner ellipse remains positioned over the limbus as defined by the physician, and the outer ellipse remains at a constant distance from the inner ellipse, even as the eye moves. Similarly, during the procedure, the controller may calculate the center or edge of each target region by adding the appropriate (x, y) offset to the identified limbus center. Advantageously, due to this feedback process, the safety and efficacy of the procedure is greatly improved.

Moreover, as an additional safety measure, the controller may define a region, referred to herein as a "forbidden zone," in the aforementioned still image. The forbidden zone encompasses the pupil of the eye, along with, typically, a portion of the eye surrounding the pupil. The forbidden zone is static, in that it is defined in terms of the field of view (FOV) of the camera, and is not adjusted even in response to detected motion of the eye. The controller may then prevent any of the treatment beams from striking the forbidden zone. Moreover, the controller may prevent the beam-directing elements from being aimed at the forbidden zone, even while the radiation source is inactive. Thus, the retina of the eye is protected from any potential (though unlikely) stray beams.

In some embodiments, the trabeculoplasty device further comprises a visible light source, and the controller is configured to cause the visible light source to flash visible light at the eye such that the visible light is on at least while each image is acquired. Advantageously, the flash of light reduces the time needed to acquire the image, such that the position of the target region calculated responsively to the image does not move significantly before the aiming beam or treatment beam is fired at the target region. Moreover, the flash may constrict the pupil of the eye, thus further protecting the retina from any potential stray beams.

Typically, the light is flashed at a sufficiently high frequency, and/or each pulse of light has a sufficiently long duration, such that the flashing is unnoticeable to the patient. Nonetheless, the total energy of the flashed light is low enough such that the light does not damage the retina.

Alternatively, to reduce the time required for image acquisition without discomforting the patient, the eye may be illuminated with near-infrared light. In addition, optionally, visible light may be flashed at the eye, such that the visible light is on while the images are acquired and/or between image acquisitions.

Embodiments of the present invention further provide a technique to facilitate positioning the trabeculoplasty device at the correct distance (or "range") from the eye. Conventionally, this type of positioning is performed by aiming two circular range-finding beams at the eye from the device, and moving the device toward or away from the eye until the two beams overlap. However, as the present inventors have observed, for several reasons, it may be difficult to use this technique for positioning the trabeculoplasty device; for example, the sclera is covered by a conjunctiva that may distort and reflect the range-finding beams, thus making it difficult to discern that the beams overlap. Hence, in embodiments of the present invention, the range-finding beams are given different respective shapes, such that the beams form a particular pattern only when the trabeculoplasty device is positioned at the correct distance from the eye. For example, the range-finding beams may be shaped as perpendicular ellipses, such that the range-finding beams form a cross over the eye only at the correct range.

In some embodiments, to reduce obstruction of the sclera by the upper eyelid, the optical unit of the trabeculoplasty device is mounted on a wedge, such that the camera and radiation source are directed obliquely upward. The patient's gaze is then directed, obliquely downward, toward the optical unit, such that the upper portion of the patient's sclera is exposed.

Although the present description relates mainly to a trabeculoplasty procedure, the techniques described herein may also be applied to automatic photocoagulation procedures, iridotomy procedures, capsulectomy procedures, lens removals, or any other relevant ophthalmological procedures. The target of the radiation may include the trabecular meshwork and/or any other suitable portion of the eye, such as the endothelial stem cells or Schlemm's canal cells of the eye. Embodiments of the present invention may be used to treat glaucoma, ocular hypertension (OHT), and other diseases.

System Description

Figure 2:
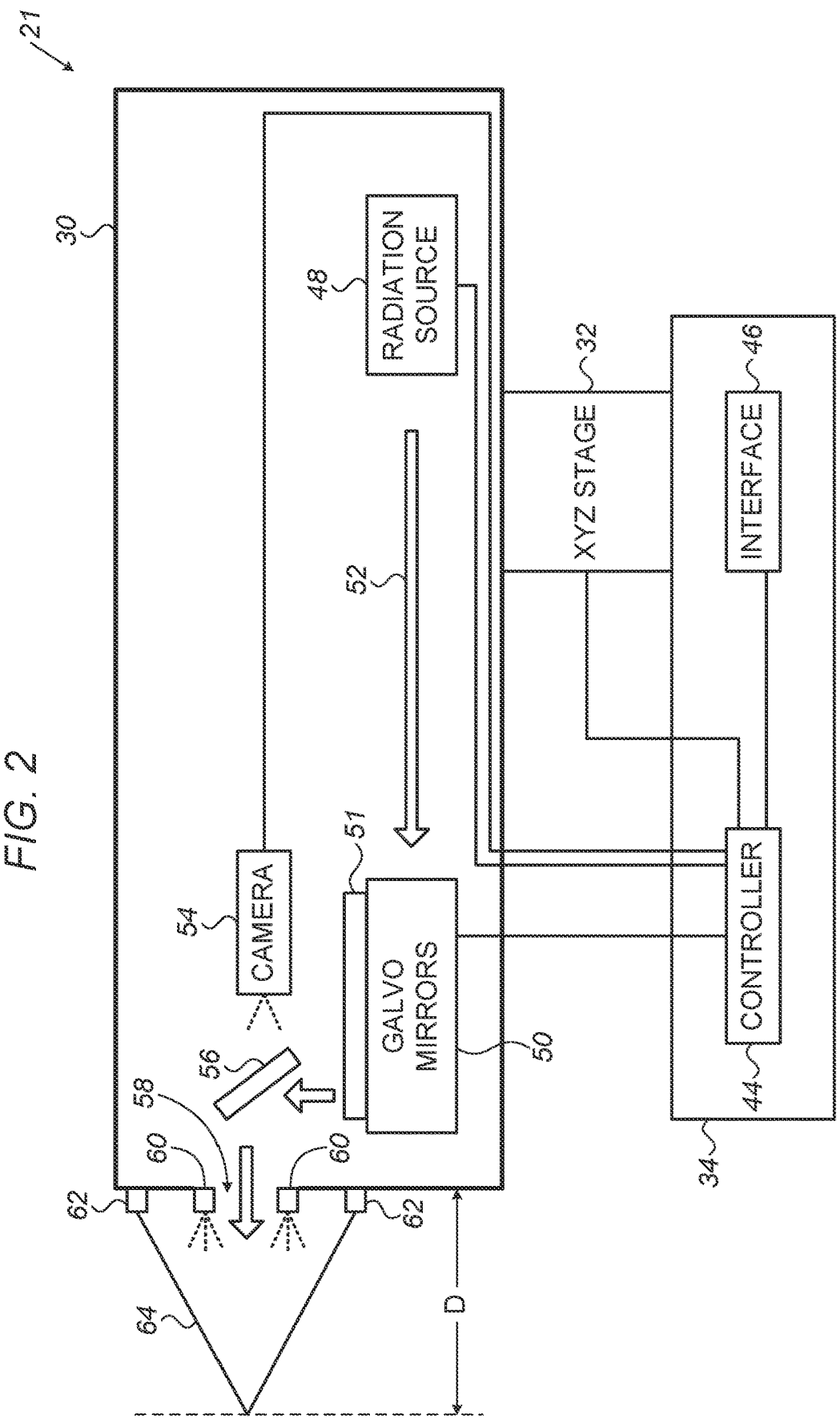
FIG. 2 is a schematic illustration of trabeculoplasty device, in accordance with some embodiments of the present invention.

Reference is initially made to FIG. 1, which is a schematic illustration of a system 20, comprising a trabeculoplasty device 21, for performing a trabeculoplasty, in accordance with some embodiments of the present invention. Reference is further made to FIG. 2, which is a schematic illustration of trabeculoplasty device 21, in accordance with some embodiments of the present invention.

Trabeculoplasty device 21 comprises an optical unit 30. Optical unit 30 comprises a radiation source 48, which is configured to irradiate an eye 25 of a patient 22 with both aiming beams and treatment beams as described herein. Optical unit 30 further comprises one or more beam-directing elements, comprising, for example, one or more galvo mirrors 50 (which may be referred to collectively as a "galvo scanner") and/or a beam combiner 56. Before the firing of each beam 52 from radiation source 48, or while the beam is being emitted, a controller 44 aims the beam-directing elements at the desired target region on eye 25 such that the beam is directed, by the beam-directing elements, toward the target region. For example, the beam may be deflected by galvo mirrors 50 toward beam combiner 56, which may then deflect the beam through an aperture 58 at the front of the optical unit such that the beam impinges on the target region. Each beam emitted by the radiation source may have an elliptical (e.g., circular) shape, a square shape, or any other suitable shape.

Typically, the radiation source comprises two lasers: one for firing aiming beams as described herein, and another for firing treatment beams as described herein. As a purely illustrative example, the treatment laser may comprise an Ekspla™ NL204-0.5K-SH laser (modified, for example, to include an attenuator, energy meter, and mechanical shutter), while the aiming laser may comprise a Laser Components™ FP-D-635-IDI-C-F laser. Typically, both the aiming beams and the treatment beams comprise visible light.

Alternatively or additionally to a laser, the radiation source may comprise any other suitable emitter configured to emit radiation belonging to any suitable portion of the electromagnetic spectrum, including, for example, microwave radiation, infrared radiation, X-ray radiation, gamma radiation, or ultraviolet radiation.

In some embodiments, each beam 52 passes through a beam expander (not shown), which expands and then re-collimates the beam, prior to reaching the galvo scanner. In such embodiments, optical unit 30 typically comprises an F-theta lens 51, configured to focus each beam subsequently to the direction of the beam by the galvo scanner.

In other embodiments, a focusing lens is disposed between the radiation source and the galvo scanner; for example, the aforementioned beam expander may comprise a focusing lens instead of a collimating lens, or the optical unit may comprise a focusing lens in addition to the beam expander. In such embodiments, each of the beams is focused by the focusing lens prior to being directed by the beam-directing elements, such that F-theta lens 51 may not be needed.

Optical unit 30 further comprises a camera 54. Before and during the procedure, camera 54 acquires multiple images of the patient's eye, typically at a relatively high frequency. Controller 44 processes these images and, in response thereto, controls radiation source 48 and the beam-directing elements, as described below with reference to FIGS. 3-4. As shown in FIG. 2, camera 54 may be positioned behind beam combiner 56, such that the camera receives light via the beam combiner.

Typically, optical unit 30 further comprises an illumination source 60 comprising, for example, one or more light emitting diodes (LEDs), such as a ring of LEDs surrounding aperture 58. In such embodiments, controller 44 may cause illumination source 60 to intermittently flash light at the eye, as further described below with reference to FIG. 4. (For ease of illustration, the connection between controller 44 and illumination source 60 is not shown explicitly in FIG. 2.)

Optical unit 30 is mounted onto an XYZ stage 32, which is controlled by a control mechanism 36, such as a joystick. Using control mechanism 36, a user of system 20, such as an ophthalmological surgeon or another physician, may position the optical unit at the appropriate position prior to treating the eye of the patient. In some embodiments, XYZ stage 32 comprises locking elements configured to inhibit motion of the stage following the positioning of the stage.

In some embodiments. XYZ stage 32 comprises one or more motors, and control mechanism 36 is connected to interface circuitry 46. As the user manipulates the control mechanism, interface circuitry 46 translates this activity into appropriate electronic signals, and outputs these signals to controller 44. In response to the signals, the controller controls the motors of the XYZ stage. In other embodiments, XYZ stage 32 is controlled manually by manipulating the control mechanism.

Typically, before the radiation source fires any beams at the eye, the user, using control mechanism 36, positions the optical unit at a predefined distance D from the eye. To facilitate this positioning, the optical unit may comprise a plurality of beam emitters 62 (comprising, for example, respective laser diodes), which are configured to shine a plurality of range-finding beams 64 on the eye, e.g., such that the angle between the beams is between 30 and 100 degrees. As further described below with reference to FIG. 3, range-finding beams 64 are shaped to define different respective portions of a predefined composite pattern, such that the predefined composite pattern is formed on the eye only when the optical unit is at the predefined distance from the eye. Hence, in response to observing the composite pattern, the user may ascertain that the optical unit is at the predefined distance.

System 20 further comprises a headrest 24, which is mounted onto a horizontal surface 38, such as a tray or table top. Headrest 24 comprises a forehead rest 26 and a chinrest 28. During the trabeculoplasty procedure, patient 22 presses his forehead against forehead rest 26 while resting his chin on chinrest 28.

In some embodiments, headrest 24 further comprises an immobilization strap 27, configured to secure the patient's head from behind and thus keep the patient's head pressed against the headrest. Immobilization strap 27 may comprise a single segment extending from the headrest at one side of the head and configured to fasten to the headrest at the other side of the head, or two segments that extend from the headrest at opposite sides of the head and are configured to fasten to one another behind the head. Optionally, the immobilization strap may comprise a sensor configured to detect when the immobilization strap is properly fastened. For example, fastening the immobilization strap may cause an electrical circuit to be closed, and the sensor may then detect the flow of electric current through the circuit and generate an output (e.g., by lighting an LED) responsively thereto.

In some embodiments, headrest 24 further comprises one or more sensors, which may be disposed, for example, on the forehead rest or chinrest. Each of these sensors may be configured to generate an output indicating whether the patient's head is resting on the headrest as required. Examples of suitable sensors include capacitive, resistive, and piezoelectric sensors. Alternatively or additionally, the headrest may comprise one or more switches or force-sensitive resistors, such as the Sparkfun™ 9375.

In some embodiments, to contain any radiation reflected by the eye, a physical block is placed around the eye. For example, a hood may be placed over the chinrest and/or over the patient's head. Alternatively or additionally, a hood may be coupled to the face of device 21.

In some embodiments, device 21 further comprises a base unit 34, which is mounted onto surface 38, and XYZ stage 32 is mounted onto base unit 34. In such embodiments, controller 44 and interface circuitry 46 may be disposed within the base unit. In other embodiments, the XYZ stage is mounted directly onto surface 38.

Typically, as shown in FIG. 1, while irradiating the patient's eye, the optical unit is directed obliquely upward toward the eye while the eye gazes obliquely downward toward the optical unit, i.e., the optical path 23 between the eye and the optical unit is oblique, rather than horizontal. For example, optical path 23 may be oriented at an angle θ of between five and twenty degrees. Advantageously, this orientation reduces occlusion of the patient's eye by the patient's upper eyelid and associated anatomy. Optionally, for additional exposure of the eye, a finger, a speculum, or another tool may be used to retract one or both of the eyelids.

In some embodiments, as shown in FIG. 1, the oblique orientation of the optical path is achieved by virtue of the optical unit being mounted on a wedge 40, which is mounted on the XYZ stage. In other words, the optical unit is mounted onto the XYZ stage via wedge 40.

Alternatively or additionally to using wedge 40, the oblique orientation of the optical path may be achieved by tilting the patient's head backward. For example, forehead rest 26 and/or chinrest 28 may comprise an adjustable-length strap, and the patient's head may be tilted backward by adjusting the length of the strap. (For example, the forehead strap may be constricted.) To facilitate this adjustment, the adjustable-length strap may comprise a worm-type drive, a hook-and-loop fastener, snaps, locking pins, knots, and/or any other suitable mechanism.

In other embodiments, the patient's head is tilted slightly forward, e.g., by angling headrest 24 (or at least chinrest 28) toward the optical unit, such that the patient's head rests more securely on the headrest.

System 20 further comprises a monitor 42, configured to display the images of the eye acquired by the camera, as described in detail below with reference to FIG. 3. Monitor 42 may be disposed at any suitable location, such as on surface 38 next to device 21. In some embodiments, monitor 42 comprises a touch screen, and the user inputs commands to the system via the touch screen. Alternatively or additionally, system 20 may comprise any other suitable input devices, such as a keyboard or a mouse, which may be used by the user.

In some embodiments, monitor 42 is connected directly to controller 44 over a wired or wireless communication interface. In other embodiments, monitor 42 is connected to controller 44 via an external processor, such as a processor belonging to a standard desktop computer.

It is emphasized that the configuration shown in FIG. 2 is provided by way of example only. Moreover, alternatively or additionally to the components shown in FIG. 2, device 21 may comprise any suitable components. For example, the device may comprise an additional illumination source, such as an LED, on which the patient may fixate during the procedure. Such an illumination source may be disposed, for example, near aperture 58 or next to the camera.

In some embodiments, at least some of the functionality of controller 44, as described herein, is implemented in hardware, e.g., using one or more Application-Specific Integrated Circuits (ASICs) or Field-Programmable Gate Arrays (FPGAs). Alternatively or additionally, controller 44 may perform at least some of the functionality described herein by executing software and/or firmware code. For example, controller 44 may comprise a central processing unit (CPU) and random access memory (RAM). Program code, including software programs, and/or data may be loaded into the RAM for execution and processing by the CPU. The program code and/or data may be downloaded to the controller in electronic form, over a network, for example. Alternatively or additionally, the program code and/or data may be provided and/or stored on non-transitory tangible media, such as magnetic, optical, or electronic memory. Such program code and/or data, when provided to the controller, produce a machine or special-purpose computer, configured to perform the tasks described herein.

In some embodiments, the controller comprises a system on module (SOM), such as the Varisite™ DART-MX8M.

In some embodiments, controller 44 is disposed externally to device 21. Alternatively or additionally, the controller may cooperatively perform at least some of the functionality described herein with another, external processor.

The Pre-Treatment Procedure

Figure 3:
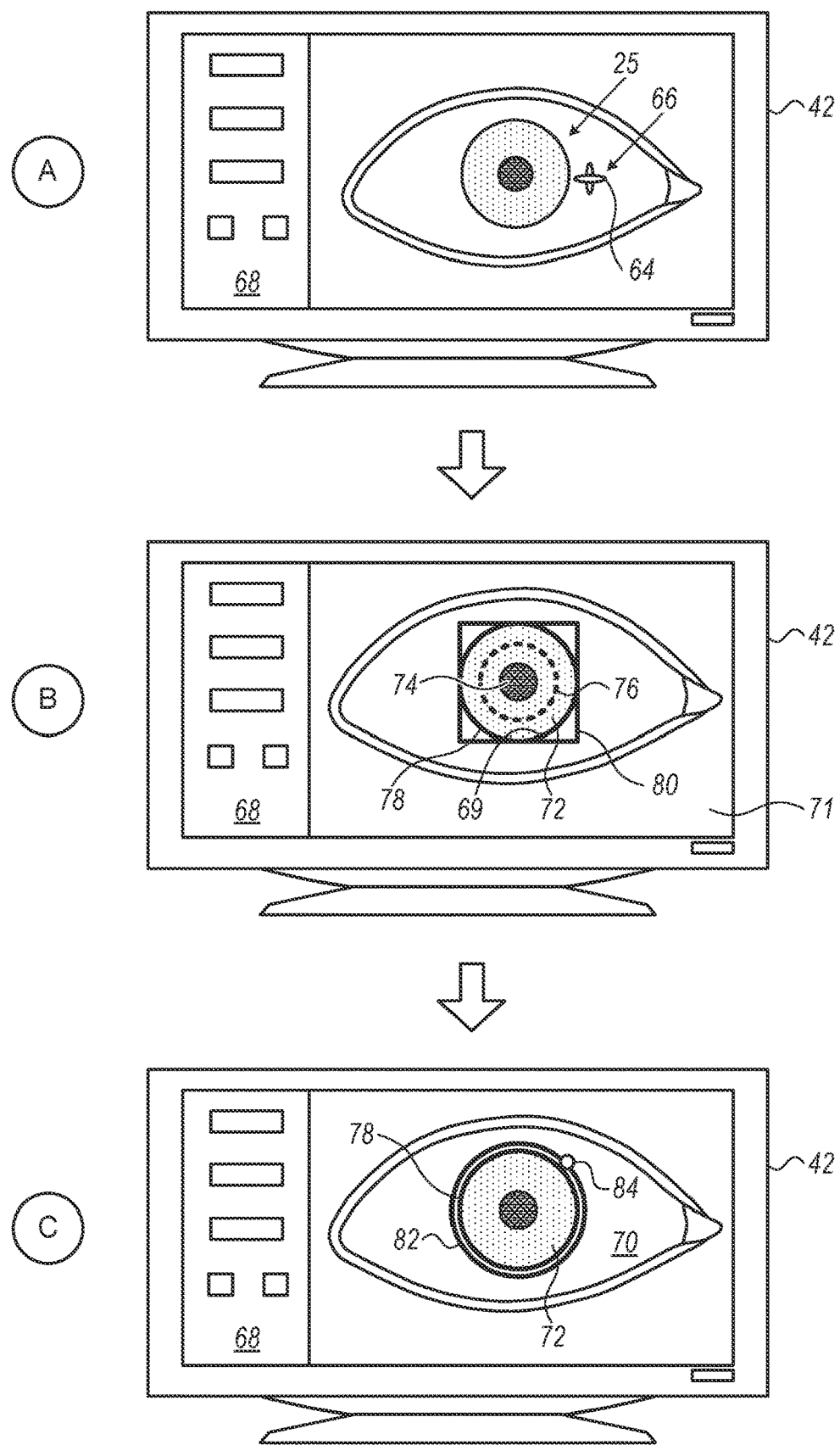
FIG. 3 is a schematic illustration of a pre-treatment procedure, in accordance with some embodiments of the present invention.

Reference is now made to FIG. 3, which is a schematic illustration of a pre-treatment procedure, in accordance with some embodiments of the present invention.

By way of introduction, the procedure illustrated in FIG. 3 includes three steps, referred to in the figure as steps A-C. For each of these steps, FIG. 3 shows an image of eye 25, which is acquired by camera 54 (FIG. 2) and displayed, by controller 44 (FIG. 2), on monitor 42. Typically, a graphic user interface (GUI) 68 is further displayed on monitor 42 beside each image. GUI 68 may include text boxes containing relevant alphanumeric data and/or instructions for the user, buttons for confirming or rejecting a particular treatment plan, and/or any other relevant widgets.

In step A, the user positions optical unit 30 (FIG. 2) such that the center of the eye is approximately at the center of the FOV of the camera. The user also positions the optical unit at the correct distance from the eye, such that the treatment beams have the proper spot size on the eye. As described above with reference to FIG. 2, this positioning is typically facilitated by range-finding beams 64, which are shaped to define different respective portions of a predefined composite pattern 66 such that pattern 66 is formed on the eye only when the optical unit is at the correct distance. Typically, the user forms the composite pattern on the sclera of the eye, near the limbus. (Typically, while the position of the optical unit is adjusted, the controller displays a live sequence of images of the patient's eye.)

For example, as shown in FIG. 3, the range-finding beams may be shaped to define two perpendicular shapes, such as two perpendicular ellipses, rectangles, or lines, which form a cross on the eye only when the optical unit is at the correct distance. Alternatively, the range-finding beams may be shaped to define two arcs or semicircles, which form a circle, or two triangles or arrowheads, which form a diamond or X shape. Any suitable optical elements such as diffractive optical elements (DOEs), holograms, or axicons may be used to facilitate generating these patterns.

In other embodiments, only a single range-finding beam is emitted, and a computer-generated pattern is superimposed over the images of the eye. When the optical unit is at the correct distance, the range-finding beam and the computer-generated pattern overlap or form composite pattern 66.

In response to observing pattern 66, the user indicates to the controller that the optical unit is at the correct distance from the eye. For example, the user may click an appropriate button on GUI 68. In response to this input, the controller proceeds to step B of the pre-treatment procedure.

In step B, the controller displays a still image 71 of the eye. Subsequently, based on input from the user, the controller identifies an elliptical (e.g., circular or almost circular) portion of the eye, such as the limbus 69 of the eye. For example, the controller may identify the portion of the eye in response to the user superimposing an elliptical marker 78 over the portion of the eye. The position of marker 78 may then be used to compute the respective positions of the treatment-beam target regions, as further described below.

For example, the controller may display, over the still image, both marker 78 and a rectangle 80 circumscribing (or "bounding") the marker. Subsequently, the user may adjust rectangle 80, e.g., by dragging the sides or corners of the rectangle using a mouse or touch screen. (In some embodiments, the system allows the user to toggle between a rough and fine adjustment of the rectangle.) In response to the user adjusting the rectangle, the controller may adjust marker 78 such that the marker remains circumscribed by the rectangle, until the marker is superimposed over the limbus as defined by the user (or over another portion of the eye). Subsequently, the user may indicate to the controller (e.g., via GUI 68) that the marker is superimposed over the limbus as defined by the user.

In some embodiments, the controller superimposes two horizontal lines tangent to the top and bottom extremities of marker 78, respectively, and two vertical lines tangent to the left and right extremities of marker 78, respectively, without necessarily causing the lines to intersect each other and thus define a rectangle. In such embodiments, the user may adjust marker 78 by dragging the lines.

Typically, prior to allowing the user to adjust marker 78, the controller, using an edge-detection algorithm or any other suitable image-processing technique, identifies the limbus in the still image and then displays marker 78 over the limbus. (It is noted that the controller may approximate the form of the limbus by any suitable shape, such as an elliptical shape aligned with the vertical and horizontal axes or rotated by any suitable angle.) Advantageously, by initializing the placement of marker 78 in this manner, the time required to adjust the marker is reduced. (Since the limbus is generally not a well-defined feature, the location of the limbus as identified by the user typically differs slightly from the location of the limbus as identified initially by the controller; hence, as presently described, the user is allowed to adjust the marker.)

Alternatively or additionally to adjusting the rectangle, the user may directly adjust marker 78 by inputting relevant parameters. For example, for an elliptical (e.g., circular) marker, the user may input the coordinates of the center of the marker and one or two diameters of the marker. Alternatively or additionally, the user may adjust the marker by adjusting an input to the limbus-identification algorithm (such as a threshold for edge detection) that is executed by the controller. As yet another option, the user may manipulate marker 78 directly.

In alternative embodiments, marker 78 is not shown at all. In such embodiments, the user may indicate the position of the limbus by dragging the rectangle or lines that would bound the marker if the marker were shown. As yet another alternative, for greater precision, a non-elliptical marker having another shape that more precisely corresponds to the shape of limbus 69 may be used instead of elliptical marker 78.

Typically, prior to the execution of the pre-treatment procedure illustrated in FIG. 3, the user (using GUI 68, or any other suitable input interface) specifies the respective positions of a plurality of target regions relative to the portion of the eye that is to be identified in step B. Alternatively, these parameters may be defined in advance, prior to use of the system by the user.

For example, the user may specify an elliptical path of target regions adjacent to the limbus, by specifying the number of target regions and the distance from the limbus (or from the center thereof) at which the center or edge of each of the target regions is to be located. Alternatively, the user may specify one or more arced paths, by specifying, in addition to the aforementioned parameters, (i) an angular span of each arc, and (ii) the location of each arc. (For example, the user may specify a 180 degree arc around the bottom or top half of the limbus, or respective 90 degree arcs at the top and bottom.) Given this input, and given the location of the limbus as indicated by the user, the controller calculates the respective positions of the target regions, typically relative to the center of the limbus as identified by the controller. (In some embodiments, the controller calculates the position of the ellipse or arc specified by the user, but does not calculate the specific positions of the target regions on the ellipse or arc until after the performance of step C, described below.)

As a purely illustrative example, the user may specify that the center or edge of each target region is to be at a distance of d1 from the limbus as marked by the user, at a different respective angle $\theta_i$ relative to the center of the limbus. The user may then, during step B, adjust marker 78 such that the center of the marker is at (x0+Δx, y0+Δy), wherein (x0, y0) is the center of the limbus as identified by the controller. In such a case, assuming that marker 78 is a circle with radius R, the controller may compute the offset from the limbus center of the center or edge of each target region as (Δx+(R+d1)cos($\theta_i$), Δy+(R+d1)sin($\theta_i$)). (It is noted that d1 may be zero, i.e., the center or edge of each target region may coincide with the limbus as marked by the user, such that the respective centers or edges (respectively) of the treatment beams impinge on the limbus as marked by the user.) Subsequently, during the procedure, as further described below with reference to FIG. 4, the controller may track the center of the limbus and, for each target region, compute the position of the region by adding this offset to the position of the center.

Typically, in step B, the controller also identifies, based on the still image, a static region 76 in the field of view (FOV) of the camera—also referred to herein as a "forbidden zone"—that includes the pupil 74 of the eye, typically along with a "buffer" that includes a significant portion of the cornea 72 of the eye surrounding pupil 74. Typically, the size of the buffer is set based on the maximum expected movement of the eye.

In some embodiments, region 76 is identified based on the location of the limbus as automatically identified by the controller or as marked by the user. For example, the controller may identify region 76 as the set of all points in the FOV located inside the limbus at more than a predefined distance from the limbus. Alternatively, for example, the controller may identify the point at the center of the limbus or the center of the pupil, and then center region 76 at this center point. In such embodiments, region 76 may have any suitable shape, such as an elliptical or rectangular shape, and may have any suitable size. The significance of region 76 is described below with reference to FIG. 4. (It is noted that region 76 is not necessarily displayed on monitor 42.)

Following step B, the controller proceeds to step C, in which the trabeculoplasty procedure is simulated. In response to viewing the simulation, the user may provide a confirmation input to the controller, e.g., by clicking an appropriate button (such as a "START" button) in GUI 68. This input confirms that the controller should proceed with the procedure.

More specifically, in step C, the controller displays a live sequence of images (i.e., a live video) of the eye, and, while displaying the sequence of images, irradiates the eye with one or more aiming beams 84, which are visible in the images. Typically, the aiming beams are red; for example, each aiming beam may have a wavelength of between 620 and 650 nm. In some embodiments, the color of the aiming beams is different from that of the treatment beams; for example, whereas the aiming beams may be red, the treatment beams may be green, having a wavelength of between 515 and 545 nm (e.g., 532 nm), for example.

While irradiating the eye with the aiming beams, the controller controls the beam-directing elements such that, if the treatment beams were to be fired, the treatment beams would impinge on the calculated target regions. Thus, the respective centers of the aiming beams may coincide, sequentially, with the center of each target region. Alternatively, if F-theta lens 51 (FIG. 2) is used, and if the color of the aiming beams is different from that of the treatment beams, chromatic aberration introduced by the F-theta lens may cause the aiming beams to be slightly offset from the target regions. Nevertheless, even in this case, the aiming beams typically impinge on at least part of each target region.

In some embodiments, the controller sweeps a single aiming beam along the eye, such that the aiming beam impinges on at least part of each target region. In other embodiments, the controller fires a plurality of aiming beams, such that each aiming beam impinges on at least part of a different respective one of the target regions.

Typically, while performing the simulation, the controller superimposes marker 78 over the portion of the eye that was identified in step B. To compensate for any movement of the eye, the controller typically identifies the center of the limbus in each of the images, and places marker 78 at the appropriate offset from the limbus. For example, if the final position of the center of marker 78 in the still image (step B) is (x0+Δx, y0+Δy), the controller may place marker 78 at an offset of (Δx, Δy) from the center of the limbus in each of the live images.

Alternatively or additionally to superimposing marker 78, the controller may superimpose, on each of the images, another marker 82 passing through (e.g., through the center of) or near each target region. The position of marker 82 may be adjusted responsively to motion of the eye, by maintaining marker 82 at the proper offset from marker 78. For example, if the center of each target region is to be at a distance of d1 from the limbus as marked by the user, marker 82 may be kept at a distance of d1 from marker 78. In some embodiments, marker 82 is a different color from that of marker 78.

Typically, while performing the simulation, the controller verifies that each of the aiming beams was properly directed by the beam-directing elements. For example, the controller may process a feedback signal from the encoders for galvo mirrors 50. Alternatively or additionally, the controller, by processing the images, may verify the respective positions of the aiming beams with respect to marker 78, marker 82, and/or any other suitable marker superimposed on each of the images. For example, the controller may verify that each aiming beam (e.g., the center of each aiming beam) overlaps marker 82, and/or that the edge of each aiming beam touches marker 78. (In the context of the present application, including the claims, the "edge" of a beam may be defined in terms of the knife-edge measure, the $1/e^2$ width measure, the full width at half maximum measure, or any other suitable measure.) As another example, the controller may verify that the center or edge of each aiming beam is positioned at the appropriate distance from marker 78.

In response to verifying the positions of the aiming beams, the controller may proceed with the trabeculoplasty procedure, provided that the user provides the aforementioned confirmation input.

In some embodiments, if the user does not confirm the simulation, the treatment is aborted. In other embodiments, the user may (e.g., via GUI 68) adjust the path followed by the aiming beams. This adjustment may be performed by returning to step B and adjusting marker 78, and/or by adjusting the distance from marker 78 at which each target region is to be located. In such embodiments, the simulation may be repeated for each new path defined by the user, until the user confirms the path.

The Treatment Procedure

In response to receiving the aforementioned confirmation input from the user, the controller treats the eye by irradiating the target regions with respective treatment beams. The peak power of the treatment beams is much higher than that of the aiming beams; furthermore, typically, the wavelength of the treatment beams is better suited for treating the trabecular meshwork of the eye, relative to the wavelength of the aiming beams.

More specifically, during the treatment, the controller continues to sweep an aiming beam through the target regions, or to fire respective aiming beams at the target regions, while acquiring images of the eye. As further described below with reference to FIG. 4, the controller verifies the position of the aiming beam in each of the images, and in response thereto, fires a treatment beam at the eye. For example, the controller may fire the treatment beam at the target region on which the aiming beam impinged, or at the next target region.

Typically, the controller causes each of the treatment beams to impinge on the eye outside region 76 (FIG. 3), also referred to herein as a "forbidden zone." (As noted above, region 76 is static, in that the region is defined in terms of the FOV of the camera, and hence does not move with the eye.) Moreover, as an extra precaution, the controller may inhibit the beam-directing elements from being aimed at (i.e., from "traveling through") region 76 even while none of the treatment beams is being fired. (Typically, the controller also applies these precautionary measures while firing the aiming beams during the pre-treatment procedure.)

Typically, while acquiring each of the images during the treatment procedure, the controller causes illumination source 60 (FIG. 2) to flash visible light (e.g., white light, red light, or green light) at the eye. By virtue of this flashing, the required exposure time of the camera may be reduced, e.g., by a factor of three or more; thus, for example, the required exposure time may be reduced from 9 ms to 3 ms. Each flash may begin before, and/or end after, the acquisition of an image. Typically, the peak average intensity over the duration of each flash is 0.003-3 mW/cm, which is generally high enough to reduce the required camera exposure time and to constrict the pupil of the eye without causing harm to the patient.

Typically, the light is flashed at a frequency that is sufficiently high such that the patient does not notice the flashing, but rather, perceives steady illumination. For example, the light may be flashed at a frequency of at least 60 Hz, such as at least 100 Hz. (in such embodiments, the duration of each flash (or "pulse") is typically less than 3 ms, such as less than 2 ms or 1 ms.) Since the frequency of the flashing may be higher than the frame rate (i.e., the frequency at which the images are acquired), some of the flashes may occur between image acquisitions. For example, the flashing frequency may be an integer multiple of the frequency at which images are acquired, such that the flashing is synchronized with the image acquisition. As a purely illustrative example, with a frame rate of 60 Hz, the flashing frequency may be 120 Hz or 180 Hz.

Alternatively, the light may be flashed at a lower frequency, but the duration of each flash may be increased such that steady illumination is perceived. For example, if the patient perceives flickering with a flashing frequency of 100 Hz and a 20% duty cycle, the duty cycle may be increased to 40% by increasing the pulse width without changing the frequency.

In some embodiments, illumination source 60 is configured to emit near-infrared light. In such embodiments, near-infrared light may be shone continuously during the treatment, or at least while the images are acquired, in order to reduce the required camera exposure time without disturbing the patient. Optionally, illumination source 60 may also flash visible light at the eye during and/or between the image acquisitions, so as to further reduce the required exposure time and/or to constrict the pupil.

Figure 4:
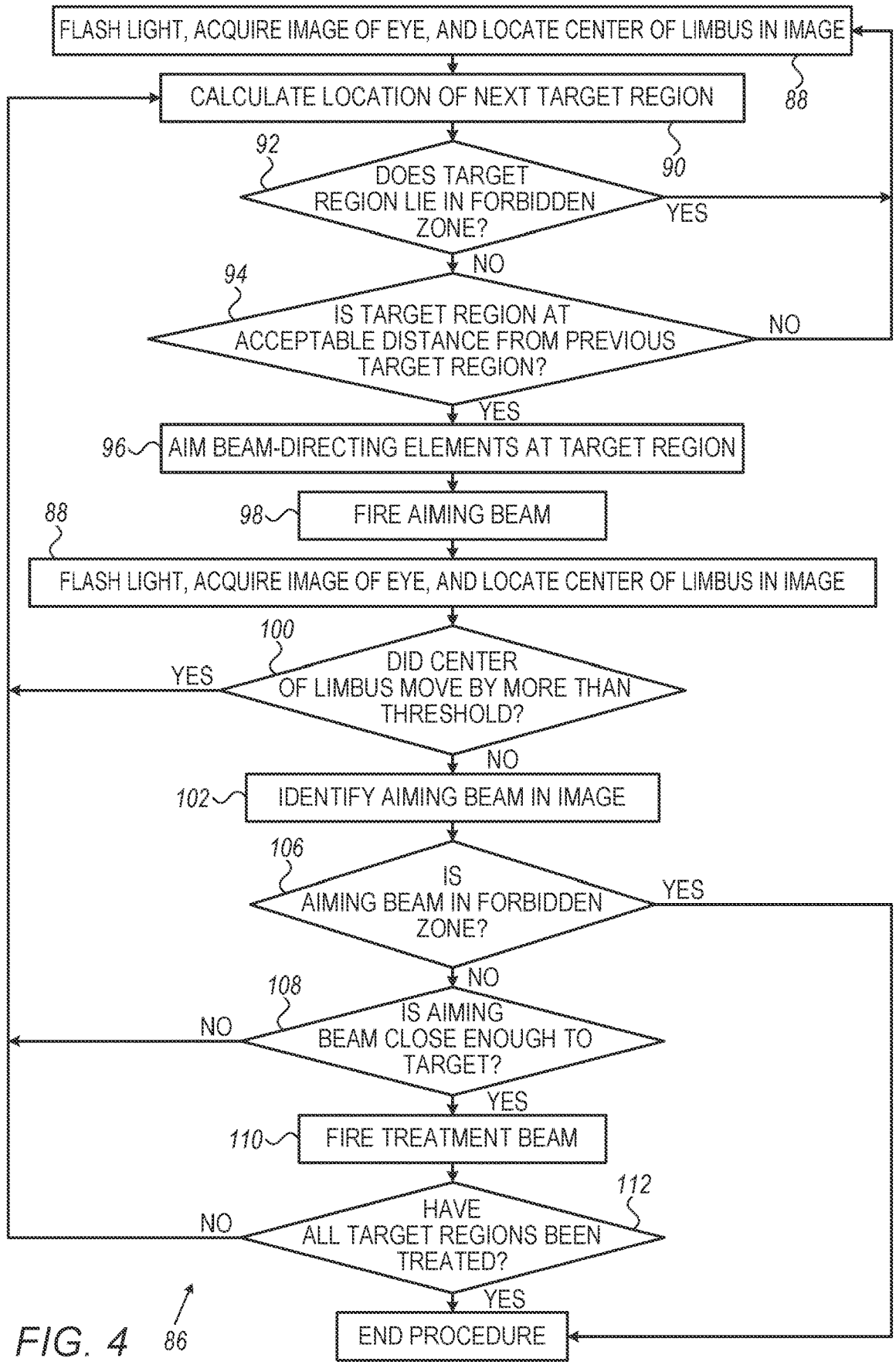
FIG. 4 is a schematic illustration of an example algorithm for performing an automated trabeculoplasty procedure, in accordance with some embodiments of the present invention.

Some further details regarding the trabeculoplasty procedure are now provided with reference to FIG. 4, which is a schematic illustration of an example algorithm 86 for performing an automated trabeculoplasty procedure, in accordance with some embodiments of the present invention.

To begin the procedure after approval of the simulated procedure by the user, the controller, at an imaging-and-locating step 88, flashes light at the eye, uses the camera to acquire an image of the eye during the flash, and locates the center of the limbus in the acquired image. Subsequently, at a target-calculating step 90, the controller calculates the position of the next target region, by adding the appropriate (x, y) offset to the location of the center of the limbus. After verifying this position, the target region is irradiated, as further described below. The controller then acquires another image, calculates the position of the next target region, verifies the position, and irradiates the target. In this manner, the controller iteratively irradiates the target regions.

More specifically, for each calculated target region, the controller checks, at a first target-checking step 92, whether the target region lies (even partly) in the forbidden zone, which, it will be recalled, is a static region in the FOV of the camera. (To perform this check, the controller does not necessarily explicitly calculate the boundaries of the target region; for example, the controller may check whether the point at the center of the target region lies more than a predefined distance—equivalent to or slightly greater than the radius of the aiming beam or treatment beam—from the border of the forbidden zone.) If not, the controller performs a second target-checking step 94, at which—provided that the target region was preceded by a previous target region—the controller checks whether the target region is at an acceptable distance from the previous target region. For example, the controller may check whether the distance between the target region and the previous target region is less than a predefined threshold, indicating that the eye is relatively still. If the target region is not at an acceptable distance from the previous target region, or if the target region is in the forbidden zone, the controller returns to imaging-and-locating step 88.

If the calculated target region passes both first target-checking step 92 and second target-checking step 94, the controller aims the beam-directing elements at the target region, at an aiming step 96. Subsequently, the controller, at an aiming-beam-firing step 98, fires an aiming beam at the beam-directing elements, such that the aiming beam is directed toward the target region by the beam-directing elements. Alternatively, a single aiming beam may be continuously emitted, such that there is no need to perform aiming-beam-firing step 98.

Subsequently, the controller performs imaging-and-locating step 88. The controller then checks, at a limbus-center-checking step 100, whether the center of the limbus moved (relative to the most-recently acquired image) by more than a predefined threshold. If yes, the controller returns to target-calculating step 90, and recalculates the location of the target region with respect to the center of the limbus. Otherwise, the controller, at an aiming-beam-identifying step 102, identifies the aiming beam in the image.

Subsequently to identifying the aiming beam, the controller checks, at a first aiming-beam-checking step 106, whether the aiming beam is in the forbidden zone. If the aiming beam is in the forbidden zone—indicating rapid movement of the eye or a failure in the system—the controller terminates the procedure. Otherwise, the controller checks, at a second aiming-beam-checking step 108, whether the distance between the aiming beam and the calculated target region is within a predefined threshold. If not, the controller returns to target-calculating step 90. Otherwise, the controller fires the treatment beam, at a treatment-beam-firing step 110, such that the treatment beam impinges on the target region.

Typically, in addition to identifying and verifying the position of the aiming beam, the controller checks each image for any obstructions that may be obstructing the target region, including, for example, an eyelid, eyelashes, a finger, growths (such as pterygium), blood vessels, or a speculum. In the event that an obstruction is identified, the target region may be shifted to avoid the obstruction. Alternatively, the target region may be skipped entirely, or the treatment procedure may be terminated.

In general, obstructions may be identified using any suitable image-processing techniques, optionally in combination with input from the user. For example, prior to the treatment procedure, the user may select (e.g., with reference to the still image) one or more portions of the eye that constitute potential obstructions. Subsequently, the controller may use template matching, edge detection, or any other suitable techniques—including, for example, identifying changes between successive images—to identify the selected portions of the eye. Such techniques may also be used to identify other static or dynamic obstructions that were not necessarily identified in advance by the user. (It is noted that the definition of "obstruction" may vary between applications; for example, whereas in some applications a particular blood vessel may constitute an obstruction, in other cases it may be desired to irradiate the blood vessel.)

Following treatment-beam-firing step 110, the controller checks, at a final checking step 112, whether all of the target regions have been treated. If yes, the controller terminates the procedure. Otherwise, the controller returns to target-calculating step 90.

Advantageously, the time between the acquisition of each image and the firing of the treatment beam is typically less than 15 ms, e.g., less than 10 ms. In some embodiments, this delay is reduced is even further, by firing the treatment beam between aiming step 96 and aiming-beam-firing step 98 (or, if a single aiming beam is continuously emitted, between aiming step 96 and imaging-and-locating step 88), instead of after second aiming-beam-checking step 108. (In such embodiments, the aiming beam is used to verify post facto that the treatment beam was fired correctly.)

In some embodiments, a separate routine executed by the controller monitors the time from each image acquisition. If this time exceeds a predefined threshold (such as a threshold between 10 and 15 ms), the treatment beam is not fired until after the next image is acquired and the target position is recalculated.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. A system, comprising:
    a radiation source;
    one or more beam-directing elements; and
    a controller, configured to:
        cause the radiation source to emit one or more aiming beams at the beam-directing elements such that the aiming beams are directed, by the beam-directing elements, toward an eye of a patient,
        verify that each of the aiming beams is properly directed by the beam-directing elements, and
        in response to verifying that each of the aiming beams is properly directed by the beam-directing elements, treat the eye by causing the radiation source to irradiate one or more target regions of the eye with respective treatment beams.

2. The system according to claim 1, wherein each of the aiming beams impinges on at least part of a respective one of the target regions.

3. The system according to claim 1, wherein the controller is further configured to display a live sequence of images of the eye while the aiming beams are emitted, and wherein the aiming beams are visible in the images.

4. The system according to claim 3, wherein the controller is further configured to receive a confirmation input from a user subsequently to the user viewing the images, and wherein the controller is configured to treat the eye in response to receiving the confirmation input.

5. The system according to claim 3, wherein the controller is further configured to superimpose a marker on each of the images, and wherein the controller is configured to verify that each of the aiming beams is properly directed by the beam-directing elements by processing the images so as to verify respective positions of the aiming beams with respect to the marker.

6. The system according to claim 5, wherein the marker passes through each of the target regions.

7. The system according to claim 5, wherein the marker is elliptical.

8. The system according to claim 5, wherein the controller is configured to verify the respective positions of the aiming beams by verifying that the aiming beams overlap the marker.

9. The system according to claim 5, wherein the controller is configured to verify the respective positions of the aiming beams by verifying that the aiming beams lie outside the marker.

10. The system according to claim 1, wherein the beam-directing elements comprise an encoder, and wherein the controller is configured to verify that each of the aiming beams is properly directed by the beam-directing elements by processing a feedback signal from the encoder.

11. A method, comprising:
    causing a radiation source to emit one or more aiming beams at one or more beam-directing elements such that the aiming beams are directed, by the beam-directing elements, toward an eye of a patient,
    verifying, by a controller, that each of the aiming beams is properly directed by the beam-directing elements, and
    in response to verifying that each of the aiming beams is properly directed by the beam-directing elements, treating the eye by causing the radiation source to irradiate one or more target regions of the eye with respective treatment beams.

12. The method according to claim 11, wherein each of the aiming beams impinges on at least part of a respective one of the target regions.

13. The method according to claim 11, further comprising displaying a live sequence of images of the eye while the aiming beams are emitted, wherein the aiming beams are visible in the images.

14. The method according to claim 13, further comprising receiving a confirmation input from a user subsequently to the user viewing the images, wherein treating the eye comprises treating the eye in response to receiving the confirmation input.

15. The method according to claim 13, further comprising superimposing a marker on each of the images, wherein verifying that each of the aiming beams is properly directed by the beam-directing elements comprises processing the images so as to verify respective positions of the aiming beams with respect to the marker.

16. The method according to claim 15, wherein the marker passes through each of the target regions.

17. The method according to claim 15, wherein the marker is elliptical.

18. The method according to claim 15, wherein verifying the respective positions of the aiming beams comprises verifying that the aiming beams overlap the marker.

19. The method according to claim 15, wherein verifying the respective positions of the aiming beams comprises verifying that the aiming beams lie outside the marker.

20. The method according to claim 11, wherein the beam-directing elements include an encoder, and wherein verifying that each of the aiming beams is properly directed by the beam-directing elements comprises verifying that each of the aiming beams is properly directed by the beam-directing elements by processing a feedback signal from the encoder.

* * * * *